United States Patent [19]

Shimokawa

[11] Patent Number: 4,915,606
[45] Date of Patent: Apr. 10, 1990

[54] STEAM STERILIZING APPARATUS FOR MUSHROOM CULTURE MEDIUM

[75] Inventor: Tsuyoshi Shimokawa, Koushoku, Japan

[73] Assignee: Kabushiki Kaisha Tiyoda Seisakusho, Koushoku, Japan

[21] Appl. No.: 234,957

[22] Filed: Aug. 22, 1988

[30] Foreign Application Priority Data

Aug. 26, 1987 [JP] Japan .......................... 62-128559[U]
Aug. 26, 1987 [JP] Japan .......................... 62-128560[U]

[51] Int. Cl.⁴ ................................................. A61L 2/00
[52] U.S. Cl. ....................................... 422/295; 422/26; 426/511; 426/521; 137/176
[58] Field of Search ................... 422/26, 116, 114, 295, 422/296, 297, 300, 27; 137/176; 426/506, 511, 521; 47/1.1; 71/5

[56] References Cited

U.S. PATENT DOCUMENTS

| | | | |
|---|---|---|---|
| 4,003,703 | 1/1977 | Montgomery, Jr. et al. | 422/26 |
| 4,203,947 | 5/1980 | Young et al. | 422/116 |
| 4,225,555 | 9/1980 | Fahvlik et al. | 422/26 |
| 4,372,916 | 2/1983 | Chamberlain et al. | 422/116 |
| 4,637,916 | 1/1987 | Hennebert et al. | 422/295 |
| 4,685,507 | 8/1987 | Schafer | 422/26 |
| 4,759,909 | 7/1988 | Joslyn | 422/116 |

Primary Examiner—Michael S. Marcus
Assistant Examiner—Gregory R. Muir
Attorney, Agent, or Firm—Ladas & Parry

[57] ABSTRACT

A culture medium used for cultivating mushrooms is sterilized by a sterilizing apparatus. The sterilizing apparatus comprises a sterilizing container in which the culture medium is placed, a steam supply pipe for supplying steam in the sterilizing container, an exhaust pipe for exhausting steam and air in the container, and a drain pipe for draining condensate from the container. The drain pipe includes a main pipe having a relatively large diameter and a bypass pipe provided with a trap. The amounts of steam supplying and exhausting and the amount of condensate draining are controlled in accordance with a predetermined mode during the sterilizing processes by regulating valve means mounted to the respective pipes. Two exhaust pipes having different exhausting capacities may be provided in consideration of environmental conditions.

3 Claims, 2 Drawing Sheets

STEAM STERILIZING APPARATUS FOR MUSHROOM CULTURE MEDIUM

BACKGROUND OF THE INVENTION

This invention relates to an apparatus for sterilizing a culture medium contained in a cultivating vessel such as wide-mouthed bottle for cultivating mushrooms such as hackberry or champignon by the use of heated steam.

In the case of cultivating mushrooms such as hackberries, they are normally placed in a cultivating vessel such as wide-mouthed bottle containing a culture medium consisting essentially of sawdust. For the cultivation of the mushrooms in this manner, the culture medium is preliminarily sterilized by using heated steam for preventing various germs or bacteria from breeding in the cultivating vessel and for facilitating the growth of the mushrooms.

One typical example of a conventional steam sterilizing apparatus for the mushroom culture medium of the character described above, is disclosed in Japanese Utility Model Laid-Open Publication (Kokai) No. 139232/1986 published Aug. 29, 1986. The known steam sterilizing apparatus comprises a sterilizing container usually of a box shape, a steam supply pipe connected to the sterilizing container, a boiler for supplying highly heated and pressurized steam to the sterilizing container, and an exhaust pipe for discharging the steam and air in the sterilizing container outwardly.

The steam supply pipe is equipped with a steam valve for adjusting the amount of supply of the steam into the container body, and the exhaust pipe is also equipped with an exhaust valve for adjusting the exhaust amount of the steam from the sterilizing container. A drain pipe is also disposed at the bottom of the sterilizing container having one end opening into the container for draining water condensed therein, and the drain pipe is equipped with a trap therein.

The steam sterilizing apparatus of this conventional type operates as follows. Highly heated and pressurized steam is supplied into the sterilizing container from the boiler through the steam supply pipe with the steam valve opened and the exhaust valve also opened, until the temperature in the sterilizing container rises to about 100° C.

After the temperature has been raised to about 100° C., the steam is continuously supplied for a period of time with the exhaust valve opened, this process usually being called a "flow-steaming process" to exhaust the air in the sterilizing container. After the flow-steaming process, the exhaust valve is closed to increase the internal pressure of the sterilizing container and to thereby increase the inner temperature to about 120° C. required for sterilizing the culture medium placed beforehand in the sterilizing container. Since the pressure in the sterilizing container is kept constant by means of a pressure adjusting valve, the temperature therein can be constantly kept at about 120° C. as long as the supply of the steam is continuously made with the exhaust valve closed. This process is a socalled "sterilizing process", and after completion of the sterilizing process carried out from a predetermined period of time, the steam valve and the exhaust valve are both closed to gradually reduce or lower the pressure and the temperature in the sterilizing container, this process being a so-called "settling process". The steam remaining in the sterilizing container is then exhausted into the atmosphere by opening the exhaust valve.

During these processes, a part of the steam supplied in the sterilizing container contacts the inner wall surfaces thereof and the culture medium and is then condensed into water, which is drained to outside the sterilizing container through the drain pipe equipped with the trap. The condensate, i.e. water, however, often includes much sawdust or other substances such as dirt. In case such condensate is drained as it is, the sawdust or other substances will be caught by the trap to finally clog it, and result in difficulty in draining the condensate through the drain pipe, and in certain extreme cases, the bottom of the sterilizing container is flooded with the condensate.

In the above described apparatus, it is not so difficult to raise the temperature in the sterilizing container to about 100° C. in the summer season or in a case where the sterilizing container is placed in an environment at which the temperature is relatively high, but in winter or in a case where the environment is of relatively low temperature, it is difficult to raise the temperature in the sterilizing container and the culture medium disposed therein to about 100° C. by supplying the steam of about 100° C., so that much time is consumed for raising and maintaining the temperature in the sterilizing process.

This difficulty may be eliminated by constructing the sterilizing container using a double-wall structure such as in medical sterilizing devices, but such structures require are costly, and are therefore not economically applicable to a sterilizing container for the culture medium for, for example, mushrooms.

SUMMARY OF THE INVENTION

An object of this invention is to eliminate defects or drawbacks of the prior art apparatus described above, and to provide an apparatus for sterilizing culture medium for cultivating mushrooms, and capable of easily and smoothly draining condensate together with dust or dirt deposited on the bottom portion of the sterilizing container.

Another object of this invention is to provide an apparatus for sterilizing culture medium for cultivating mushrooms capable of effectively sterilizing the culture medium with heated steam regardless of seasons or a temperature of the environmental atmosphere.

These and other objects can be achieved, according to this invention, by providing an apparatus for sterilizing a culture medium for cultivating mushrooms comprising a sterilizing container in which culture medium for cultivating mushrooms is placed, steam supply pipe means for supplying heated steam into the sterilizing container, exhaust pipe means for exhausting steam and air in the sterilizing container into the atmosphere, and a drain pipe arrangement for draining condensate from a bottom portion of the sterilizing container, and draining pipe arrangement comprising a drain pipe having one end opened in the bottom of the sterilizing container and being provided with a drain valve therein, and a bypass pipe connected to the drain pipe so as to bypass the drain valve and provided with a trap therein, the drain pipe having a diameter greater than that of the bypass pipe.

In a preferred embodiment, the bypass pipe is arranged above the drain pipe at a level substantially equal to or slightly higher than the bottom surface of the sterilizing container.

According to the construction of the sterilizing apparatus set forth above, the steam supplied in the sterilizing container contacts the inner walls of the container and the culture medium disposed therein and is then condensed as a condensate on the bottom floor of the sterilizing container. The drain valve is opened during the temperature increasing process and the flow-steaming process as described hereinbefore, so that the condensate together with a relatively voluminous sawdust, dirt and the like is drained through the drain pipe having a relatively large diameter. The drain valve is closed during the following settling process, and the condensate containing relatively small amount of dirts and the like is drained through the bypass pipe provided with the trap. However, as the sawdust and dirt have been substantially drained in the previous processes, the trap is never clogged, and the operation of the sterilizing apparatus can be easily and smoothly performed.

In a further preferred embodiment, the steam supply pipe is provided with a steam valve for regulating the flow rate of the steam, and first and second exhaust pipes are arranged each provided with an exhaust valve for regulating the exhaust flow rate of the steam and air. These supply and exhaust pipes are so designed that the steam exhausting capacity of the first exhaust pipe is made smaller than the steam supplying capacity of the steam supply pipe and the sum of steam exhausting capacities of the first and second exhaust pipes is made greater than the steam supplying capacity of the steam supply pipe.

According to this arrangement, during the temperature increasing process, the highly heated steam is supplied into the sterilizing container with the steam valve opened and the first exhaust valve also opened, while the second exhaust valve is closed. Since the exhausting capacity of the first exhaust pipe is made smaller than the supply capacity of the steam pipe under the atmospheric pressure, the pressure in the sterilizing container increases to above the atmospheric pressure. Accordingly, the temperature of the steam increases to above 100° C., the boiling point of water, whereby the temperature can be easily increased in the sterilizing container even in winter or when the container is placed in a cold environment. When the temperature in the sterilizing container has increased to about 100° C., the flow-steaming process starts with the second exhaust valve opened. Accordingly, the sterilizing apparatus can easily and effectively sterilize the culture medium even when the sterilizing apparatus is located in a cold environment.

Preferred embodiments according to this invention will be described further in detail with reference to the accompanying drawings.

DESCRIPTION OF THE PREFERRED EMBODIMENTS

Figure 1:
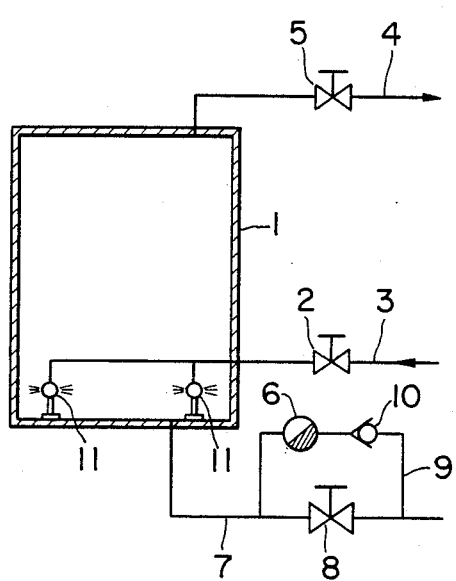
FIG. 1 is a schematic diagram of an embodiment of a culture medium sterilizing apparatus according to this invention.

FIG. 1 is a schematic diagram of one embodiment of an apparatus for sterilizing a culture medium according to this invention, and the apparatus comprises a steam sterilizing container 1 of a box shape to be later described in detail, a steam supply pipe 3 through which highly heated and pressurized steam is supplied into the steam sterilizing container 1 from, for example, a boiler, not shown, and an exhaust pipe 4 through which air and steam in the sterilizing container 1 is exhausted into the atmosphere. A steam valve 2 and an exhaust valve 5 are provided in the steam supply pipe 2 and the exhaust pipe 4, respectively, so as to regulate the flow rate of the fluid passing therethrough. The steam supplied in the steam sterilizing container 1 is ejected thereinto through nozzle holes of pipe members 11 connected to the supply pipe 3 to spread in the interior of the container 1. The steam supply capacity of the steam supply pipe 3 is made substantially equal to the exhaust capacity of the exhaust pipe 4. The sterilizing apparatus further comprises a drain pipe 7 having one end opened in the bottom portion of the container 1 through which condensate, i.e. water, is drained. A drain valve 8 is provided in the drain pipe 7 for regulating the flow rate of the condensate flowing through it. A bypass pipe 9 is connected to the drain pipe 7 so as to bypass the drain valve 8. A trap 6 and a check valve 10 are disposed in the bypass pipe 9, which has a diameter smaller than that of the drain pipe 7. The check valve 10 may be dispensed with should the occasion demand. It is desirable that the location of the trap 6 is at essentially the same level as, or at a slightly higher level than, that of the location of the bottom surface of the sterilizing container 1.

A culture medium for cultivating mushrooms is sterilized in the following manner by using the sterilizing apparatus having the construction described above with reference to FIG. 1.

The steam valve 2 is first opened, with the exhaust valve 5 also opened to supply highly heated and pressurized steam into the sterilizing container 1, in which the culture medium contained in a cultivating vessel is disposed on a rack, until the temperature in the interior of the sterilizing container 1 reaches about 100° C. The heated and pressurized steam is continuously supplied for a predetermined period of time to perform so-called a "flow-steaming process" with the exhaust valve 5 still opened to exhaust air in the sterilizing container 1 through the exhaust pipe 4.

During these heating and flow-steaming processes, the highly heated steam supplied through the supply pipe 3 contacts the inner wall of the sterilizing container 1 and cultivating vessels, not shown, each containing a culture medium which has not yet been sufficiently heated, and the steam contacting these members is then condensed as condensate, which drops to the bottom of the container 1.

A relatively large amount of the condensate is produced and drained together with substances such as sawdust which have dropped on the bottom floor of the sterilizing container 1 through the drain pipe 7. The drain pipe 7 has a relatively large diameter and the drain valve 8 can have a simple on-off construction, so that the condensate containing sawdust mixed therewith is easily and smoothly drained outwardly of the sterilizing container 1 without clogging the drain pipe 7 and the drain valve 8 with the sawdust. Furthermore, since the bypass pipe 9 provided with the trap 6 has a fine diameter and is located about the drain pipe 7, condensate including a large amount of sawdust and the like does not substantially intrude into the bypass pipe 9.

After the flow-steaming process has been completed, the exhaust valve 5 is closed to increase the inner pressure of the sterilizing container 1 whereby the temperature therein is increased to about 120° C. which is required for sterilizing germs or bacterias contained in the culture medium such as sawdust. This process is called a "sterilizing process" and the drain valve 8 is closed during this sterilizing process.

The condensate which has dropped during this sterilizing process on the bottom floor of the sterilizing container 1 is drained into the drain pipe 7 and exhausted through the bypass pipe 9 because the drain valve 8 is closed. The condensate which is drained in the sterilizing process is of relatively small amount in comparison with the condensate which is drained during the heating and flow-steaming processes. Moreover, relatively large amount of, or voluminous substances such as sawdust or dirt have already been removed during the heating and flow-steaming processes through the drain pipe 7 having a large diameter, so that the trap 6 is never clogged with such substances when the condensate is drained through the bypass pipe 9.

After the sterilizing process, the valves 2, 5 and 8 are all closed and the final settling process is carried out.

Figure 2:
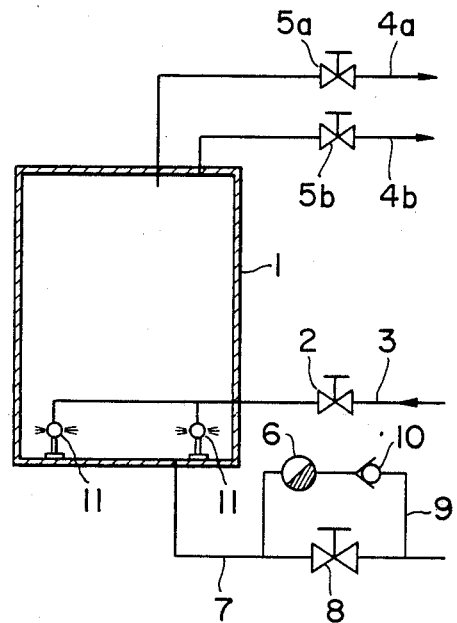
FIG. 2 is a schematic diagram of a modified embodiment of the sterilizing apparatus shown in FIG. 1.

FIG. 2 is a schematic diagram of a preferred modification of the sterilizing apparatus shown in FIG. 1, the modification being made in consideration of a case where the sterilizing container 1 is used in a cold winter season or placed in an environment of a relatively low temperature.

The modification is of substantially identical construction to that of FIG. 1, except that two exhaust pipes 4a and 4b are provided instead of one exhaust pipe 4 in the embodiment shown in FIG. 1, and accordingly, the like reference numerals are added to the members or elements corresponding to those shown in FIG. 1.

The first and second exhaust pipes 4a and 4b are equipped respectively with first and second exhaust valves 5a and 5b for regulating the exhaust amounts of air and steam in the sterilizing container 1. The exhaust pipes 4a and 4b are so constructed that the exhaust capacity of one exhaust pipe, for example, the first exhaust pipe 4a, is made smaller than the supply capacity of the steam supply pipe 3 under the atmospheric pressure and the sum of the exhaust capacities of both the exhaust pipes 4a and 4b is made greater than the supply capacity of the steam supply pipe 3.

Figure 3:
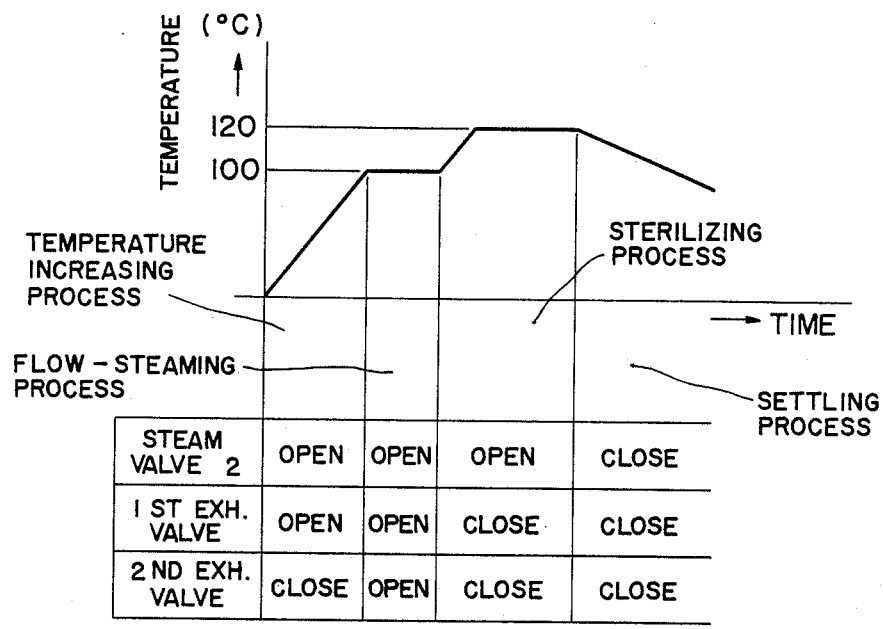
FIG. 3 is a graph representing a relationship between the temperature variations in a sterilizing container and open-close states of respective valves during the respective processes of the sterilization.

The sterilizing apparatus shown in FIG. 2 operates in the manner described with reference to FIG. 3.

During the heating or temperature increasing process, the highly heated steam is supplied into the sterilizing container 1 through the steam supply pipe 3 with the steam valve 2 opened and the first exhaust valve 5a also opened, while the second exhaust valve 5b is closed. Although the steam supplied in the sterilizing container 1 is exhausted through the first exhaust pipe 4a, the exhaust capacity of the first exhaust pipe 4a is made smaller than the supply capacity of the steam supply pipe 3 under the atmospheric pressure, so that the pressure in the sterilizing container 1 is easily increased to above the atmospheric pressure. The temperature of the steam is accordingly raised over 100° C., the boiling point of water under atmospheric pressure, whereby it is easy to increase the temperature in the interior of the sterilizing container to about 100° C. This is not the case with the apparatus of FIG. 1 wherein, in cold seasons, steam supplied into the container 1 through the pipe 3 tends to flow away through the exhaust pipe 4.

When the temperature in the sterilizing container 1, has increased to about 100° C., the flow-steaming process starts at which the second exhaust valve 5b is opened to exhaust the steam and air in the sterilizing container 1, through the first and second exhaust pipes 4a and 4b, while the steam valve 2 is being opened.

During the sterilizing process succeeding the flow-steaming process, the first and second exhaust valves 5a and 5b are closed and only the steam valve 2 is opened, and these valves are all closed during the next settling process. Since these sterilizing process and the settling process are substantially the same as those referred to with respect to the sterilizing apparatus shown in FIG. 1, the details thereof will not be described further.

It should also be understood that the modified sterilizing apparatus is also provided with the drain pipe 7 including the bypass pipe 9 having substantially the same construction as that of the sterilizing apparatus shown in FIG. 1 and attains substantially the same functions as those of the latter.

According to the modified embodiment, the sterilizing apparatus can easily and effectively sterilize culture medium placed in the sterilizing container 1 even in winter or when the container 1 is located in a cold environment.

Figure 4:
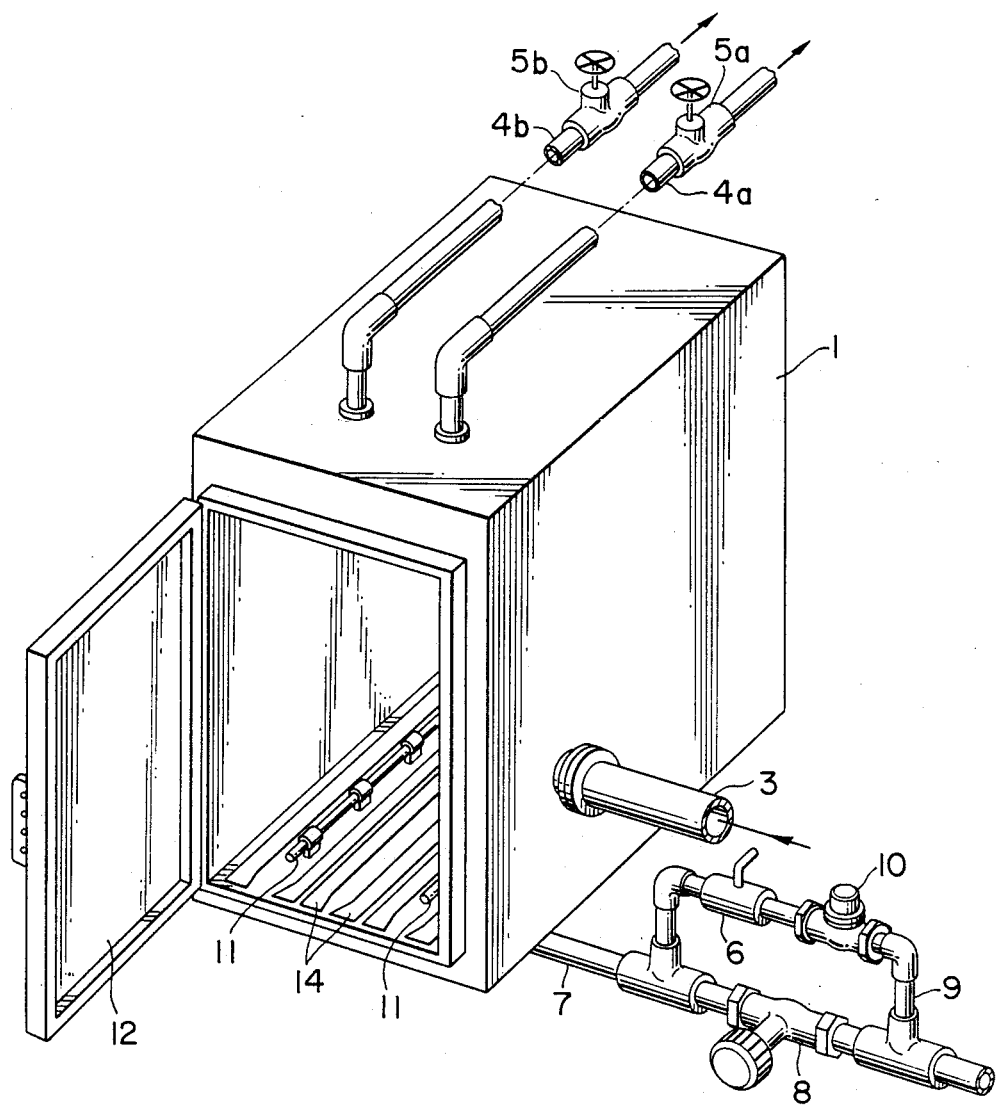
FIG. 4 is a perspective view of a culture medium sterilizing apparatus as one typical example of that shown in FIG. 2.

For further understanding of this invention, FIG. 4 shows a perspective view of a typical example of a sterilizing apparatus of the type shown in FIG. 2, in which like reference numerals are added to elements or members corresponding to those shown in FIG. 2 or 1.

Referring to FIG. 4, a sterilizing container 1 is formed as a rectangular box provided with a door 12, in which a rack, for example, not shown, is placed, and a plurality of cultivating vessels such as wide-mouthed bottles each containing culture medium such as sawdust are placed on the rack beforehand.

Sliding rails 14 may be provided on the bottom floor of the sterilizing container 1 for easy insertion of the rack therein, and any other shape of the sterilizing container may be used.

It should also be understood that this invention is not limited to the described embodiments and various other changes or modifications may be made without departing from the spirit or scope of the appended claims. For example, two steam supply pipes may be provided in a parallel arrangement for suitably regulating the amount of supply of the steam into the sterilizing container.

What is claimed is:

1. An apparatus for sterilizing a culture medium for cultivating mushrooms comprising:

a sterilizing container in which a culture medium for cultivating mushrooms is placed;

means connected to said container for supplying heated steam into said sterilizing container;

means connected to said container for exhausting steam and air in said sterilizing container into the atmosphere; and means connected to a bottom of said container for draining condensate from said bottom of said sterilizing container, said draining means comprising a drain pipe having one end opened in the bottom of said sterilizing container, said drain pipe having a drain valve therein for regulating flow rate of the condensate and a bypass pipe connected to said drain pipe so as to bypass said drain valve, said bypass pipe being arranged above said drain pipe at a level substantially equal to or slightly higher than the bottom surface of the sterilizing container, and having a trap therein, said drain pipe having a diameter greater than that of said bypass pipe.

2. The apparatus according to claim 1 wherein said steam supply means comprises a steam supply pipe provided with a steam valve therein, and said exhaust means comprises an exhaust pipe provided with an exhaust valve therein.

3. The apparatus according to claim 1 wherein said steam supply means comprises a steam supply pipe provided with a steam valve therein, and said exhaust means comprises first and second exhaust pipes respectively provided with first and second exhaust valves therein, steam exhaust capacity of said first exhaust pipe being smaller than steam supplying capacity of said steam supply pipe and sum of steam exhausting capacities of said first and second exhaust pipes being greater than the steam supplying capacity of said steam supply pipe.

* * * * *